United States Patent

Lee et al.

[11] B  3,989,667
[45] Nov. 2, 1976

[54] OLEFINIC SILOXANES AS PLATINUM INHIBITORS

[75] Inventors: Chi-Long Lee; Ollie W. Marko, both of Midland, Mich.

[73] Assignee: Dow Corning Corporation, Midland, Mich.

[22] Filed: Dec. 2, 1974

[21] Appl. No.: 528,966

[44] Published under the second Trial Voluntary Protest Program on February 24, 1976 as document No. B 528,966.

[52] U.S. Cl. .................. 260/46.5 UA; 260/46.5 G; 260/46.5 H; 260/448.2 Q; 260/825
[51] Int. Cl.² ........................................ C08G 77/04
[58] Field of Search ............... 260/46.5 UA, 46.5 H, 260/46.5 G, 448.2 H, 448.2 Q, 825, 2 S

[56] References Cited
UNITED STATES PATENTS

| | | | |
|---|---|---|---|
| 3,445,420 | 5/1969 | Kookootsedes et al. | 260/37 |
| 3,697,473 | 10/1972 | Polmanteer et al. | 260/46.5 UA |

*Primary Examiner*—Lewis T. Jacobs
*Attorney, Agent, or Firm*—Roger H. Borrousch

[57] ABSTRACT

Olefinic siloxanes which are inhibitors for platinum catalyst can be made by the reaction of secondary or tertiary acetylenic alcohols with siloxanes having silicon-bonded-hydrogen atoms. These olefinic siloxanes inhibit the platinum catalyst such that it will not catalyze the addition of SiH to aliphatic unsaturation at room temperature and does not inhibit the reaction at elevated temperatures. These olefinic siloxanes contain from 3 to 10 siloxane units with a total of at least three units from at least one RHSiO and/or $R_2HSiO_{0.5}$, at least one

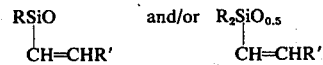

and the remaining siloxane units being $R_3SiO_{0.5}$, $SiO_2$ or $RSiO_{1.5}$ but no more than three units of any one of these siloxane units. An example of such an olefinic siloxane is

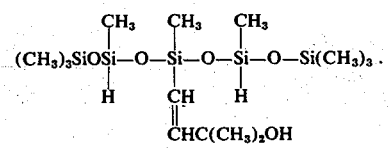

26 Claims, No Drawings

OLEFINIC SILOXANES AS PLATINUM INHIBITORS

BACKGROUND OF THE INVENTION

1. Field of the Invention

This invention relates to polyorganosiloxanes having both olefinic radicals bonded to the silicon atoms and hydrogen atoms bonded to the silicon atoms.

2. Description of the Prior Art

Platinum catalysts have been combined with olefins to make complexes which are more resistant to poisoning and have greater reactivity as disclosed in U.S. Pat. No. 3,159,601. It is therefore totally unexpected that certain olefinic siloxanes would provide the opposite effect of inhibiting the platinum catalyst activity at room temperature but permitting its activity to be effective at elevated temperatures.

Also it is known that acetylenic materials will inhibit platinum catalysts as described in U.S. Pat. No. 3,445,420 issued May 20, 1969 to Gust. J. Kookootsedes and Edwin P. Plueddemann. However, it was not known that the reaction product of acetylenic materials with siloxane compounds having silicon-bonded-hydrogen atoms would provide a useful material which would inhibit the platinum catalyst activity at room temperature and not at elevated temperatures. Only recently, Randolph G. Niemi in an application entitled "Crosslinker-Platinum Catalyst-Inhibitor and Method of Preparation Thereof" filed on even date herewith and assigned to the same party, discovered heating at 50° to 90°C. for 10 to 30 hours in a closed system a mixture of a siloxane having silicon-bonded-hydrogen atoms, a platinum catalyst and thereafter removing unreacted acetylenic alcohol by stripping at reduced pressure at room temperature a complex reaction product could be obtained which functioned as an inhibitor at room temperature for the platinum catalyst, as a crosslinker for aliphatically unsaturated containing siloxane polymers and a platinum catalyst. However, Niemi was unable to isolate any particular species which functioned as an inhibitor for the platinum catalyst and could only use his reaction product as a combination of crosslinker and platinum catalyst which did not have catalytic activity at room temperature but would become active at elevated temperature. Although Niemi's reaction product functioned and was useful in making compositions which could be heat cured when the reaction product was combined with polymers having two or more organic substituents having aliphatic unsaturation, Niemi could not alter the ratio of crosslinker, platinum catalyst and inhibitor once a reaction product was made. Thus, it was an inflexible system and a more desirable approach was indicated.

SUMMARY OF THE INVENTION

An object of this invention relates to a polyorganosiloxane which is a platinum catalyst inhibitor at room temperature but not at elevated temperatures.

This invention relates to a polyorganosiloxane having an average of 3 to 10 siloxane units, at least one SiH containing siloxane unit and at least one siloxane unit having an olefinic radical which is the addition product of SiH and a secondary or tertiary acetylenic alcohol.

DESCRIPTION OF THE INVENTION

This invention relates to a polyorganosiloxane consisting essentially of from 3 to 10 siloxane units in which (a) at least one siloxane unit is selected from the group consisting of

and (b) at least one siloxane unit is selected from the group consisting of

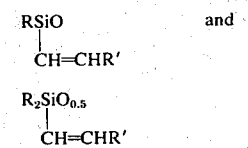

where the sum of siloxane units in (a) and (b) is equal to at least three siloxane units, (c) any remaining siloxane units being selected from the group consisting of

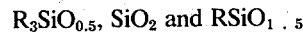

where each siloxane unit of (c) does not exceed three siloxane units, where R is a monovalent radical selected from the group consisting of hydrocarbon radicals and perfluoroalkylethylene radicals, both having no more than six carbon atoms and R' is a monovalent hydrocarbon radical having a secondary or tertiary hydroxy substitution and having no more than ten carbon atoms.

The polyorganosiloxanes of this invention can have from 3 to 10 siloxane units, preferably from 5 to 10 siloxane units. These siloxane units can have at least one a. RHSiO or $R_2HSiO_{0.5}$ unit and at least one b.

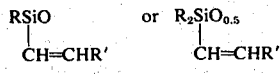

unit wherein the sum of the (a) and (b) units is at least 3. If there are other siloxane units, they can be c. $R_3SiO_{0.5}$, $SiO_2$ or $RSiO_{1.5}$ or combinations thereof wherein no single type of unit exceeds three. In the above unit formulae R represents monovalent hydrocarbon radicals, such as methyl, ethyl, propyl, isopropyl, pentyl, butyl, hexyl, phenyl, cyclohexyl or cyclopentyl and monovalent perfluoroalkylethylene radicals, such as, 3,3,3-trifluoropropyl, β-perfluoroethylethylene and β-perfluorobutylethylene. In these unit formulae, R' represents monovalent hydrocarbon radicals having a secondary or tertiary hydroxy substitution and no more than 10 carbon atoms, such as $-C(CH_3)_2OH$, $-C(CH_2CH_3)(CH_3)OH$, $-C(C_6H_5)(CH_3)OH$,

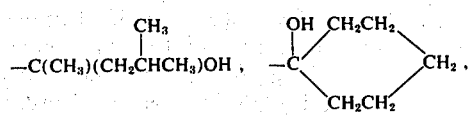

$-CH(CH_3)OH$,

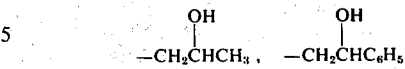

and $-CH_2C(CH_3)_2OH$

The polyorganosiloxanes of this invention are best prepared by continuously passing a mixture of an acetylenic alcohol, a platinum catalyst and a siloxane compound having at least three silicon-bonded-hydrogen atoms through a heating means wherein the mixture is heated above 100°C. and above the temperature at which the reaction product no longer inhibits the reaction under sufficient pressure to maintain the reaction mixture in the liquid state and recovering the polyorganosiloxane of this invention. This method is more fully described by Floyd A. Bergstrom, Chi-Long Lee and Myron T. Maxson in a copending application Ser. No. 528,961, filed Dec. 2, 1974, entitled "Method of Preparing A Platinum Catalyst Inhibitor" filed on even date herewith and assigned to the same party, which is hereby incorporated by reference.

Other methods for preparing the polyorganosiloxanes of this invention are known, such as the method of heating a mixture of an acetylenic alcohol, platinum catalyst and a siloxane having at least three silicon-bonded hydrogen atoms per molecule for 16 hours at 70°C. and then removing the unreacted acetylenic alcohol by stripping at room temperature under reduced pressure and thereafter distilling the remainder to obtain polyorganosiloxanes as defined herein. This method is described in the application by Niemi cited above. This method is characterized by a low yield, gellation on distillation and a danger of exploding.

Another method of making the polyorganosiloxanes of this invention is to inject a mixture of acetylenic alcohol and a siloxane having at least three silicon-bonded-hydrogen atoms into the injection port of a gas liquid chromatograph where the injection port is coated with a platinum catalyst. The chromatograph column is heated to 350°C. and a polyorganosiloxane of this invention is recovered. This method although giving higher yields than the method of Niemi, has disadvantages which are not suitable for commercial operations. These disadvantages are observed when larger columns are used, and include, decreased yields and column plugging caused by gellation. This method is described by Chi-Long Lee and Ollie W. Marko in a copending application Ser. No. 528,959, filed Dec. 2, 1974, entitled "Method of Preparing Olefinic Siloxane by GLC" filed on even date herewith and assigned to the same party.

Still another method for making the polyorganosiloxanes of this invention is described by Chi-Long Lee and Myron T. Maxson in a copending application Ser. No. 528,960, filed Dec. 2, 1974, entitled "Tube Method For The Preparation of Olefinic Siloxane Compounds" filed on even date herewith and assigned to the same party. This method uses a heated tube into which is injected in an inert carrier gas, such as helium, a mixture of acetylenic alcohol, platinum catalyst and a siloxane having at least three silicon-bonded-hydrogen atoms per molecule. The tube is heated at a temperature of 300° to 400°C. The reaction product exiting from the tube is cooled by either a single condenser or a multiple condenser series. The single condenser requires distillation to recover the desired polyorganosiloxane of this invention. The multiple condenser series uses a series of condensers at different temperatures wherein the desired polyorganosiloxane can be recovered without distillation. Although this method gives high yields, the tube plugged during continuous use and the temperature was sufficiently high and the residence times long enough to cause considerable decomposition.

All of the above methods can be used to prepare the polyorganosiloxanes of this invention, however, the first method described is the best method for the production of large quantities of product.

Preferred polyorganosiloxanes are those having at least 5 siloxane units, at least one RHSiO unit, at least one

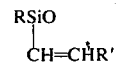

unit and two siloxane units of $$R_3SiO_{0.5}$$

where R' has a tertiary hydroxy substitution. Of these siloxanes the species which are preferred are those where R' is $$-C(CH_3)_2OH$$

R is methyl and there is either two units of RHSiO and one unit of

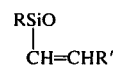

or one unit of RHSiO and two units of

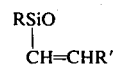

The polyorganosiloxanes of this invention are useful as inhibitors for platinum catalysts. The reaction of silicon-bonded hydrogen atoms with aliphatic unsaturation is known to be catalyzed by platinum catalysts at room temperature. Thus, when a vinyl containing siloxane polymer is mixed with a silicon compound containing silicon-bonded hydrogen atoms in the presence of platinum catalysts, a reaction occurs and if the ratio of vinyl to SiH is proper the composition cures at room temperature to a coherent solid, such as an elastomer or resin. This room temperature reactivity has forced manufacturers to use this type of reaction for products stored in two or more packages to prevent premature curing. However, there are some known materials which will inhibit the activity of platinum catalysts at room temperature but not at elevated temperatures and thus products could be stored in one package. However, the incompatibility in siloxane mixtures, wrinkling of the surface on cure and volatility of some of these inhibitors, such as the acetylenic compounds, have promoted the search for more desirable platinum catalysts inhibitors which can be used to make compositions of aliphatically unsaturated compounds, and SiH compounds catalyzed with platinum catalysts which can be stored in one package without the above described disadvantages. The polyorganosiloxanes of this invention provide such useful compositions.

This invention also relates to a curable organosilicon composition comprising (1) an organosilicon polymer having an average of from one to three groups per silicon atom selected from the group consisting of monovalent hydrocarbon radicals, aliphatic-unsaturation-free monovalent halohydrocarbon radicals, and cyanoalkyl radicals, there being an average per molecule of (1) of at least two monovalent hydrocarbon radicals containing aliphatic unsaturation, the remaining valences of the silicon atoms of the said organosilicon polymer being satisfied by divalent radicals selected from the group consisting of divalent oxygen atoms, divalent hydrocarbon radicals, divalent hydrocarbon ether radicals and divalent haloarylene radicals, said divalent radicals linking silicon atoms, (2) an organosilicon compound containing silicon-bonded hydrogen atoms, there being in addition an average of up to two monovalent organic radicals per silicon atom selected from the group consisting of monovalent hydrocarbon radicals free of aliphatic unsaturation, monovalent halohydrocarbon radicals free of aliphatic unsaturation and cyano radicals, the remaining valences of the silicon atoms being satisfied by divalent radicals selected from the group consisting of divalent oxygen atoms, divalent hydrocarbon radicals free of aliphatic unsaturation, divalent hydrocarbon ether radicals free of aliphatic unsaturation and divalent haloarylene radicals, said divalent radicals linking silicon atoms, there being an average of at least two silicon-bonded hydrogen atoms per molecule of (2), the sum of the average number of aliphatic unsaturated monovalent radicals per molecule of (1) and the average number of silicon-bonded hydrogen atoms per molecule of (2) is at least 4, (3) a platinum catalyst in an amount of at least 0.1 part by weight platinum per one million parts by weight of the combined weights of (1) and (2), and (4) a polyorganosiloxane consisting essentially of from 3 to 10 siloxane units in which (a) at least one siloxane unit is selected from the group consisting of $$RHSiO \text{ and } R_2HSiO_{0.5}$$

and (b) at least one siloxane unit is selected from the group consisting of

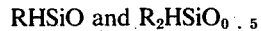

where the sum of siloxane units in (a) and (b) is equal to at least three siloxane units, (c) any remaining siloxane units being selected from the group consisting of $$R_3SiO_{0.5}, SiO_2 \text{ and } RSiO_{1.5}$$

where each siloxane unit of (c) does not exceed three siloxane units, where R is a monovalent radical selected from the group consisting of hydrocarbon radicals and perfluoroalkylethylene radicals, both having no more than six carbon atoms and R' is a monovalent hydrocarbon radical having a secondary or tertiary hydroxy substitution and having no more than ten carbon atoms.

Organosilicon compound (1) can be a resin, a fluid or a substantially non-flowing high polymer such as conventionally used in silicone rubber manufacture. Any monovalent hydrocarbon radical, halohydrocarbon radical or cyanoalkyl radical that can be used with organosilicon compounds as stated above is operable in component (1). Examples of monovalent hydrocarbon radicals that can be used include, for example, alkyl radicals such as methyl, ethyl, isopropyl, tert-butyl, octadecyl and myricyl; cycloalkyl radicals such as cyclopentyl and cyclohexyl; aralkyl radicals such as benzyl and 2-phenylethyl; aryl radicals such as phenyl, tolyl, xylyl, naphthyl, xenyl and anthracyl; and radicals containing aliphatic unsaturation such as vinyl, allyl, methallyl, ethynyl, butadienyl, cyclopentenyl, m-vinylphenyl and the like.

Any monovalent halohydrocarbon radical and cyanoalkyl radical can be used in (1), and include, for example, chloromethyl, 3,3,3-trifluoropropyl, 2,3-dibromocyclopentyl, iodophenyl, dichloronaphthyl, 2-cyanoethyl, 2-cyanopropyl, and omega-cyanooctadecyl.

In component (1) there must be an average per molecule of at least two radicals containing aliphatic unsaturation. These radicals enter into the curing reaction discussed below. More than two said radicals can be present, but a minimum of two (average per molecule) is necessary to obtain a cure to a coherent solid. When the average number of aliphatically unsaturated radicals per molecule is more than two, a correspondingly tighter cure is obtained.

The monovalent organic radicals in (1) can be the same or different. In addition, the aliphatically unsaturated radicals can be the same or different. As well, organosilicon compound (1) can be a copolymer, mixture of copolymers, mixture of monomers and polymers, mixtures of monomers and copolymers and the like.

The remaining valences of the silicon atoms in organosilicon compound (1) are satisfied by divalent oxygen, divalent hydrocarbon radicals, divalent hydrocarbon ether radicals and divalent haloarylene radicals. Any one or more of the said divalent linkages can be present in component (1).

Examples of divalent radicals that can be used in component (1) include, for example, hydrocarbon radicals such as

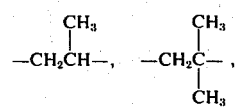

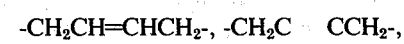

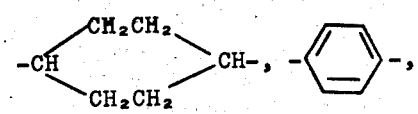

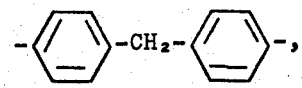

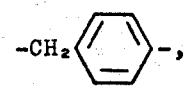

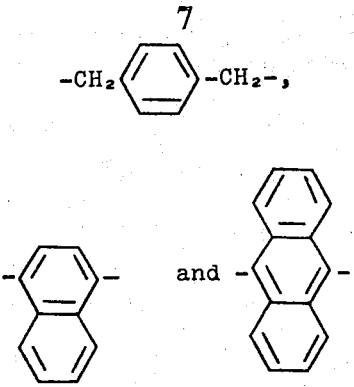

hydrocarbon ether radicals such as -CH₂CH₂OCH₂CH₂-, -CH₂CH₂CH₂OCH₂CH₂- and

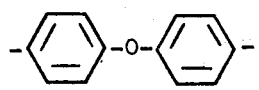

and haloarylene radicals such as

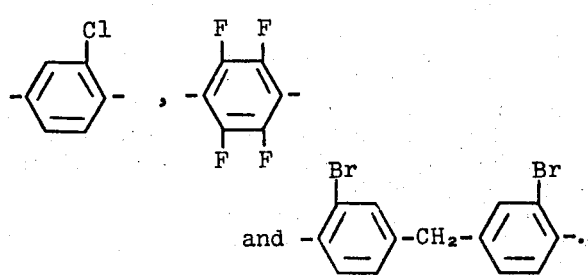

Any of the divalent linkages stated above can be present in component (1). However, where the average number of silicon atoms per molecule is greater than three, it is preferred when use of the finished product will include both extremely high and extremely low temperature exposure, that at least 50 percent of the divalent linkages be oxygen. This is not necessary, however, particularly when component (1) is a cyclic material.

Preparation of materials that can be component (1) are well known in the art. The monovalent radicals can be attached, for instance, be either the so-called "direct process," or via Grignard reaction, or in some cases by a pseudo Friedel-Crafts reaction. Other reactions normally used to introduce organic radicals can, of course, be also used. Silicon-bonded oxygen is introduced by hydrolysis of a hydrolyzable group on silicon (such as halogen, alkoxy or acyloxy), as is well known in the art. Divalent organic radicals can be introduced via Wurtz-type synthesis, Grignard, direct process, etc. The preparations of compounds suitable for use as component (1) are well known in the art and need not be recited herein.

Organosilicon compound (2) can be any organosilicon compound having silicon-bonded hydrogen atoms. It can contain two or more silicon-bonded hydrogen atoms per molecule and in addition an average of up to two monovalent radicals per silicon atom, as set forth above. These can include, for example, alkyl radicals such as methyl, ethyl, isopropyl, tert-amyl, octadecyl and myricyl; cycloalkyl radicals such as cyclopentyl and cyclohexyl; aralkyl radicals such as benzyl, β-phenylethyl and xylyl; and aryl radicals such as phenyl, tolyl, xenyl, naphthyl and anthracyl. In addition, mono- valent halohydrocarbon radicals such as chloromethyl, 3,3,3-trifluoropropyl, α, α, α-trifluorotolyl, bromophenyl and 2,3-dibromocyclopentyl can be present in component (2). Also, cyanoalkyl radicals such as cyanoethyl and cyanobutyl can also be present. The organic radicals can be alike or different. Component (2) can be a homopolymer, a copolymer, a monomer or mixture of two or more of the foregoing, provided only that each is free of aliphatic unsaturation and each contain an average per molecule of at least two silicon-bonded hydrogen atoms.

The remaining valences of the silicon atoms of component (2) are satisfied from divalent oxygen, divalent hydrocarbon radicals free of aliphatic unsaturation (e.g. -CH₂-, -(CH₂)₁₈-, -CH₂CH(CH₃)-, -CH₂C(CH₃)₂-,

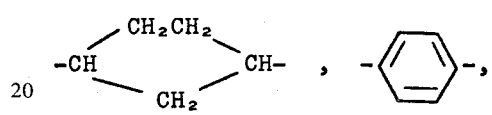

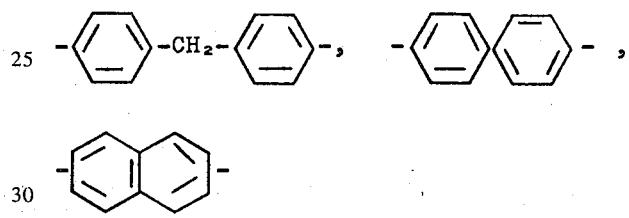

etc.), divalent hydrocarbon ether radicals free of aliphatic unsaturation (e.g., -CH₂CH₂OCH 2CH₂-, -CH₂CH₂CH₂OCH₂CH₂-,

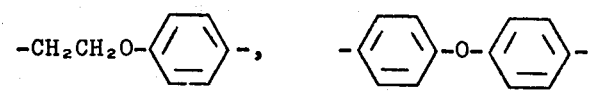

etc.), and divalent haloarylene radicals (e.g.,

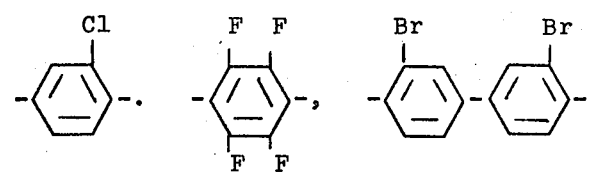

etc.). Any one or more of the above said divalent linkages can be present in component (2). As with component (1), when the average number of silicon atoms per molecule of (2) is greater than three it is preferred that at least 50 percent of the above divalent linkages be oxygen. This is not necessary, however, especially when component (2) is a cyclic material.

Preparation of materials that come within the definition of component (2) are well known in the art, and many examples of such materials are available commercially. Thus, recitation of methods of manufacture of these materials would be redundant herein. When either component has the defined quantity greater than 2.0, selection of the other component on this basis is irrelevant. It should be understood, of course, that the higher the sum of these quantities, the more highly crosslinked can be the cured composition.

The molar ratio of aliphatically unsaturated radicals in (1) to the silicon-bonded hydrogen atoms in (2) can in some cases be an important consideration. Where it is important, the ratio of these two should be preferably between 0.67 and 1.5. However, there are many instances wherein a balance of these two quantities is unimportant. For example, if a component (1) has, say, an average of six aliphatically unsaturated groups per molecule, the use of equal molar amounts of silicon-bonded hydrogen atoms may well give a cure too highly crosslinked for the desired end use. Thus, less than, sometimes much less than, the equal molar amount of SiH would be used to provide the desired degree of cure. However, when maximum stability is required it is desirable to match the molar quantities of silicon-bonded hydrogen atoms in (2) to the aliphatically unsaturated radicals in (1).

Platinum compound (3) can be any of the known forms, ranging from platinum as such or as deposited on carriers such as silica gel or powdered charcoal, to platinic chloride, salts of platinum and chloroplatinic acid. Any of these forms will function in the instant curing system. A preferred form of platinum is the chloroplatinic acid either as the commonly obtainable hexahydrate or the anhydrous form, on account of its easy dispersability in organosilicon systems and its non-effect on color of the mixture. Additional platinum compounds which include,

platinum bromides, a complex of platinous halide and an olefin such as ethylene, propylene, butylene, cyclohexene and styrene, $Pt(CH_3CH)_2Cl_2$, $\{Pt(CH_3CN)_2(CH_3)_4\}Cl_2$,
$Pt(NH_3)_2Cl_2$,     $K\{PtCl_3CH_2CH_2CH_2OH\}$,
$PtBr_2(C_2H_4)_2$
$K\{PtBr_3(C_2H_4)\}$, $PtCl_2(C_2H_4)$, $(CH_3)_2C=CH_2.PtCl_2$,
$H_2Pt(CN)_4.5H_2O$,         $H\{PtCl_3(CH_3CN)\}$,
$Pt(NH_3)_2(CNS)_2$,
$PtCl_2.PCl_3$, $\{Pt(NH_3)_4 . PtCl_4\}$,
$PtCl_2\{P(CH_2CH_3)_3\}_2$, $PtCl_2.P(OH)_3$,
$PtCl_2.P(OCH_2CH_3)_3$, $PtCl_2.\{P(OCH_2CH_3)_3\}_2$,
$Pt(OOCH_2SCH_2CH_3)_2$, $Pt(CN)_3$, $(CH_3)_4Pt$,
$(CH_3)_3Pt-Pt(CH_3)_3$,

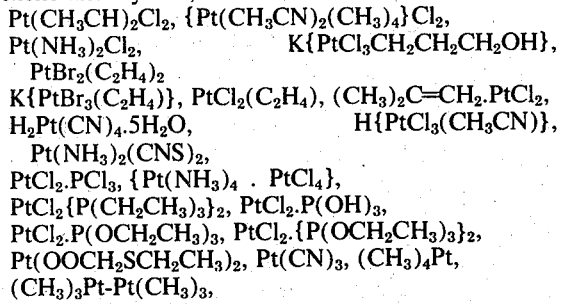

$PtCl_2CO$ and $PtBr_2CO$.

There should be at least 0.1 part by weight platinum per one million parts by weight of the combined total weight of (1) and (2). However, since impurities in the system may easily poison this small quantity of catalyst, it is preferred to employ from 1 to 20 parts per million, platinum. A greater amount of the platinum can be used, but does affect the requirement of component (4) below, and economic considerations suggest the lower amounts mentioned.

The addition of the polyorganosiloxane (4) to a composition comprising (1), (2) and (3) slows down the rate of cure at room temperature of completely prevents a cure at room temperature over long periods of time such as greater than 3 months, but at temperatures in excess of 70°C. the inhibiting effect of the polyorganosiloxane observed at room temperature disappears and a normal curing rate is realized. The cure of the curable composition can be retarded at room temperature for short periods of time or for very long periods of time by the proper amount of polyorganosiloxane. No exact amount of polyorganosiloxane can be suggested to give a specified storage life at room temperature.

The rate of cure at temperatures up to 60°C. will depend upon the ratio of polyorganosiloxane to platinum, the form of the platinum catalyst, the nature of the polyorganosiloxane, the nature and amounts of ingredients (1) and (2) and the presence or absence of other non-essential ingredients. Polyorganosiloxanes added in small amounts such as 0.1 weight percent based on the weight of the curable composition provide increased pot life in all systems, but, in most cases, do not fully retard the reaction at room temperature and in larger amounts such as 3 weight percent polyorganosiloxane, they provide completely inhibited cures at room temperature as indicated by a shelf life of greater than 6 months. However, some systems are completely inhibited at room temperature at one mole polyorganosiloxane to one mole of platinum while others may require 10, 20, 50 or 1000 moles of polyorganosiloxane per one mole of platinum to completely inhibit the system at room temperature. The amount of polyorganosiloxane is therefore dependent upon the desired use, and the nature of the system. The skilled worker should therefore determine the optimum level for each system.

The use of a polyorganosiloxane can completely prevent room temperature cure of the present curable organosilicon composition or the polyorganosiloxane can be used to slow down the rate of cure at room temperature. Slowing down the rate of cure at room temperature can be extremely useful such as wherein a particular combination of (1), (2) and (3) would cure in four hours at room temperature, the same combination with the proper amount of polyorganosiloxane would require 24 hours to cure. This extra time before cure would allow the user a longer time to use the mixture for coating, dipping, etc., before any of the mixture cured. The inhibiting effect can be negated by heating the composition above 70°C. whereby the composition cures. To obtain rapid curing the curable organosilicon compositions should be preferably heated above 100°C.

The components of this invention can be mixed in any order. While the addition of the platinum without the polyorganosiloxane will cause the beginning of interaction of components (1) and (2), the extent of reaction in a few minutes time at ordinary temperatures is negligible, at which time the polyorganosiloxane will normally have been added. In systems where even this small amount of interaction might be deleterious, the polyorganosiloxane can be added before the platinum. One method of mixing is to premix components (1) and (3), premix components (2) and (4), and then combine these two mixtures. Another method is to add the polyorganosiloxane to components (1) and (2) and then add (3). However, a set order of addition of the ingredients is not necessary to the functioning of this curing system.

The system can be mixed just prior to use (contemplated cure) or can be mixed and stored for later use. One or more of the components can be omitted, provided only that when components (1), (2) and (3) are present, component (4) must also be present. In addition, the storage of a mixture of components (2) and (3) alone or a mixture of components (3) and (4) alone is not preferred because undesirable alternate reactions can occur. Thus, components (1), (2) and (4) can be stored together and component (3) added later, or (1), (3) and (4) to which (2) is added later, etc. Although various packaging and storing systems can be prepared, the advantage of the present invention is that all the ingredients can be conveniently packaged and stored in one container without fear of premature curing in the package.

The curing reaction is that of addition of an SiH of (2) to an unsaturated radical on silicon of (1). This is a well-known reaction, catalyzed by many other materials in addition to platinum. The addition of SiH to allyl on silicon serves to illustrate the reaction as follows:

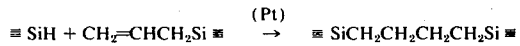

It is noteworthy that no byproducts are formed in the curing reaction. Thus, it is not necessary to cure the system under pressure as is the case when a curing system produces byproducts which are volatile. Further, it is unnecessary to carefully postbake the cured composition, as is necessary with most other heat activated curing systems now used in silicones. It is already well known that a curing system involving SiH and aliphatically unsaturated radicals need not be employed in a closed system. It is also well recognized that neither the extent of cure nor rate of cure are inhibited by air or components thereof.

In addition to the recited components, other materials can be present in a composition utilizing this curing catalyst system. Such materials as are ordinarily used in organosilicon compositions, such as fillers (carbon black, silica aerogels, silica soots, treated silicas, alumina, clays, metal oxides, metal carbonates, metal silicates, etc.), pigments to impart certain colors to the material, rubber additives such as compression set aids, plasticizers (both organosilicon and organic), etc., can be added to the instant composition. Materials that are known to poison platinum catalysts should of course be excluded, but these are not normally included in organosilicon compounds designed to be cured by heat activated curing catalysts.

The instant composition can be used for any application requiring a resin or rubber where heat activated curing is possible. One will immediately recognize the tremendously wide variety of applications herein included. The instant curing system can be activated in closed or open systems, in thin or thick sections and under pressure and at atmospheric pressure with equal ease merely by the application of heat above about 70°C., there being complete freedom from the undesirable sponging associated with some curing systems when pressure is not used, and freedom from uncured surface, obtained particularly with organic peroxides, when the composition is cured in the open exposed to the atmosphere. Thus, advantages of this particular system include excellent thick-section cure, absence of air-inhibition, and therefore uniform cure throughout the sample. In addition, where desired, the system can serve to control (slow down) the rate of cure of a platinum catalyzed SiH- unsaturated aliphatic-on-silicon room temperature cure.

Particularly useful curable organosilicon compositions for many of the above uses are those having 45 to 75 inclusive weight percent of (1), 0.5 to 10 inclusive weight percent of (2), 20 to 50 inclusive weight percent of a filler, where the weight percentages are based on the combined weights of (1), (2) and filler.

The following examples are presented for illustrative purposes and should not be construed as limiting this invention which is properly delineated in the claims.

EXAMPLE 1

In a one liter, 3-neck, round bottom flask equipped with a condenser, thermometer and mechanical stirrer, a mixture of 200 grams of a siloxane of the formula (I) $(CH_3)_3SiO\{(CH_3)HSiO\}_3Si(CH_3)_3$, 49 grams of 3-methyl-1-butyn-3-ol and 5 parts by weight platinum per one million parts by weight of composition (p.p.m.) was heated for 16 hours at 70°C. The resulting product was stripped of unreacted ingredients at reduced pressure and 50°C. The ramaining material was vacuum distilled and a small amount of an olefinic siloxane compound hereinafter referred to as the mono-adduct, having two trimethylsiloxy units, two methylhydrogensiloxane units and one siloxane unit of the formula (II) 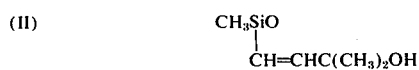

was found which had a boiling point of 104° to 105°C. at 1.0 mm of mercury. Another olefinic siloxane hereinafter referred to as the di-adduct, was also found having a boiling point of 151° to 152°C. at 1.0 mm of mercury and having two trimethylsiloxy units, one methylhydrogensiloxane unit and two siloxane units of formula (II).

EXAMPLE 2

A mixture was prepared by combining 0.8 mole of 3-methyl-1-butyn-3-ol, one mole of siloxane of formula (I) and 0.125 p.p.m. platinum in the form of a platinum catalyst complex of chloroplatinic acid hexahydrate and 1,3-divinyl-1,1,3,3-tetramethyldisiloxane containing 0.63 weight percent platinum. A closed system with pressurizing equipment, a heating bath with coil through which the liquid reaction mixture was passed, a cooling unit and appropriate pressure and temperature indicators was used. A polydimethylsiloxane fluid having a viscosity of one centistoke was pumped through the system until the operating conditions were reached, including, temperature, pressure and residence time in the heating unit. The temperature of the stream at the point where the coil left the heating bath was maintained at 300°C., the pressure was 28.12 kilograms per square centimeter (400 p.s.i.) and the residence time of the liquid mixture in the heating bath was 28.9 seconds. The reaction mixture was continuously passed through the system, cooled and collected. The product mixture was identified by mass spectroscopy and nuclear magnetic resonance and amounts determined by gas liquid chromatography (GLC) and the various species and their amounts were observed. The percent conversion was determined by integrating the area under the GLC curve and the sum of the areas for the mono-adduct, di-adduct and tri-adduct divided by the sum of the areas for the mono-adduct, di-adduct, tri-adduct and unreacted siloxane of formula (I) and then multiplied by 100 gave the percent conversion. The product showed a conversion of 43.8 percent. The amount of mono-adduct was 61.7 percent, the amount of di-adduct was 34.5 percent and the amount of tri-adduct was 3.8 percent. The amount of adducts was determined by dividing the area under the GLC curve for a particular adduct by the sum of the areas for the three adducts and multipling by 100. The areas under the GLC cure are directly related to the weight of ingredients in the mixture. The product mixture was stripped of unreacted starting materials which could be recycled and the remaining product was the mixture of adducts which were distilled to provide individual adducts or was used as a mixture. The adducts were as follows wherein the formulae shown are for illustrative purposes and do not indicate the exact position of all the olefinic radicals in the molecule for each adduct. There will be mixtures of different structural isomers for the mono and di adducts present.

Mono-adduct

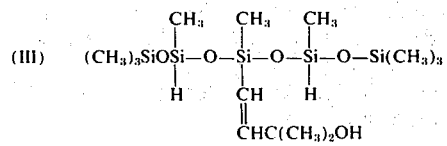

Di-adduct

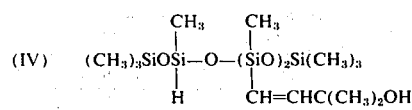

Tri-adduct

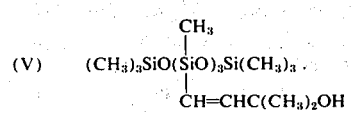

The amount of decomposition of materials was found to be about one weight percent.

EXAMPLE 3

The method of Example 2 was followed using the platinum catalyst in the amount of 2 p.p.m. platinum, a temperature of 190° to 192°C., a pressure of 16.87 kilograms per square centimeter (240 p.s.i.), a residence time of six minutes and equal molar amounts of acetylenic alcohol and siloxane of formula (I).

A first mixture used 3,5-dimethyl-1-hexyn-3-ol which resulted in a 52 percent conversion with 52 percent mono-adduct, 42 percent di-adduct and 5 percent tri-adduct where the adducts had formulae as shown in Example 2 except the olefinic siloxane units had a formula

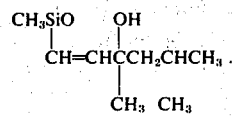

A second mixture used 3-methyl-1-pentyn-3-ol which resulted in a 47 percent conversion with 54 percent mono-adduct, 38 percent di-adduct and 7 percent tri-adduct where the adducts had formulae as shown in Example 2 except the olefinic siloxane units had a formula

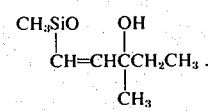

EXAMPLE 4

The distilled mono-adduct as prepared in Example 1 was used in a platinum catalyzed composition to inhibit the catalytic activity of the platinum. A base composition was prepared by mixing 74.6 parts by weight of a phenylmethylvinylsiloxy endblocked polydimethylsiloxane having a viscosity of about 450 centistokes at 25°C., 19.2 parts by weight of five micron quartz, 2.8 parts by weight of fume silica, 0.4 parts by weight lampblack, 0.8 parts by weight zinc oxide powder and 2.2 parts by weight of a hydroxyl endblocked polymethylphenylsiloxane having about 4 weight percent hydroxyl radicals. Curable compositions were prepared by mixing varying amounts of mono-adduct as indicated in Table A with 400 parts by weight of the above base composition, 25 parts by weight of a trimethylsiloxy endblocked polyorganosiloxane having an average of 10 silicon atoms per molecule, an average of three dimethylsiloxane units per molecule and an average of five methylhydrogensiloxane units per molecule, and 7 p.p.m. of platinum in the form of a complex platinum catalyst mixture of an ester-alcohol solvent mixture, chloroplatinic acid hexahydrate, symmetrical tetramethyldisiloxane and symmetrical divinyltetramethyldisiloxane, having about 0.4 weight percent platinum. The curable composition was prepared by thoroughly mixing the base composition and platinum catalyst, thoroughly mixing the polymethylhydrogensiloxane and mono-adduct and then mixing these two blends. One gram samples of each curable composition in an open container was placed in an oven at various temperatures and the cure times were recorded and were the times required for the sample to become a coherent solid elastomer. The room temperature sample was the remaining portion after the one gram samples were removed. After nine months shelf aging at room temperature, samples of Composition E were again heated at various temperatures to determine if the composition had changed on shelf aging. The results were as shown in Table A.

Table A

| Curable Composition Reference | Mono-adduct, Parts by weight | Cure Times | | | | | at room Temperature, days |
|---|---|---|---|---|---|---|---|
| | | at 150°C., minutes | at 100°C., minutes | at 70°C., hours | at 50°C., hours | at 37.8°C., days | |
| A | 0.0 | — | — | — | — | — | 1 hour |
| B | 1.0 | — | — | — | — | — | 6 |
| C | 2.0 | — | — | — | — | — | 8 |
| D | 4.0 | 1 | 8 | 4 | 31 | 5.49 | 90 |
| E | 8.0 | 1.5 | 16 | 7 | 120 | 14 | >365 |

Table A-continued

| Curable Composition Reference | Mono-adduct, Parts by weight | Cure Times | | | | | |
|---|---|---|---|---|---|---|---|
| | | at 150°C., minutes | at 100°C., minutes | at 70°C., hours | at 50°C., hours | at 37.8°C., days | at room Temperature, days |
| F* | 8.0 | — | 15.5 | 5 | 168 | 12 | — |

*after shelf aging 9 months.

EXAMPLE 5

A curable composition was prepared as described in Example 4 using a base composition prepared by mixing 100 parts by weight of phenylmethylvinylsiloxy endblocked polydimethylsiloxane having a viscosity of about 450 centistokes at 25°C. and 100 parts by weight five micron quartz. The curable composition was then prepared as described by Example 4, E., except the platinum was in an amount of about 3 p.p.m. in the form of a complex platinum catalyst prepared from chloroplatinic acid hexahydrate and symmetrical divinyltetramethyldisiloxane having about 0.65 weight percent platinum. Samples of about 450 grams were heated at various temperatures, some open containers and some sealed containers as indicated in Table B, and the skin-over-time and cure times were observed. The skin-over-time was the time required for a cured skin to form on the surface of the sample and the cure time was as defined in Example 4 where the complete sample became a coherent solid elastomer. The results were as shown in Table B. The samples were open unless indicated as closed in Table B. The cure time was also determined for two gram samples placed in aluminum weighing dishes and cured at various temperatures.

Table B

| Temperature, °C., | Skin-over-time | Cure Time | Cure Time, 2-g. Sample |
|---|---|---|---|
| 150 | 12 minutes | 30 minutes | 45 seconds |
| 100 | 30 minutes | 60 minutes | 14 minutes |
| 70 | 5 hours | 24 hours | 5 hours |
| 50 | 9 days | — | 4 days |
| 50 (sealed) | 14 days | — | — |
| 37.8 | 42 days | — | 14 days |
| RT* | >365 days | — | >365 days |
| RT (sealed) | >365 days | — | — |

*RT = room temperature.

EXAMPLE 6

A base composition as described in Example 5 was used to prepare curable compositions by mixing 100 parts by weight base composition, 6 parts by weight of a trimethylsiloxy endblocked polyorganosiloxane having methylhydrogensiloxane units as defined in Example 4, 3 p.p.m. platinum as described in Example 5 and 2 parts by weight of adduct as defined in Table C where curable composition A used the mono-adduct as described by formula (III) and curable composition B used a mixture of 86 weight percent di-adduct as described by formula (IV) and 14 weight percent tri-adduct as described by formula (V). The cure times were determined by heating two gram samples in aluminum weighing dishes at various temperatures. The results were as shown in Table C.

Table C

| Temperature, °C. | Cure Times | |
|---|---|---|
| | Composition A | Composition B |
| 100 | 19 minutes | 21 minutes |
| 70 | 4.75 hours | 7 hours |
| 51 | 2 days | 3.5 days |
| 37.8 | 6 days | 18 days |

EXAMPLE 7

Curable compositions were prepared by mixing 63 parts by weight of phenylmethylvinylsiloxy endblocked polydimethylsiloxane having a viscosity of about 450 centistokes at 25°C., 33 parts by weight 5 micron quartz, 4.87 parts by weight of trimethylsiloxy endblocked polyorganosiloxane having methylhydrogensiloxane as described in Example 4, 12 p.p.m. platinum as described in Example 5 and the amount of adduct as defined in Table D. Single species adducts were obtained by distillation of reaction product of Example 2. The results were as shown in Table D where the cure times were obtained at various temperatures.

Table D

| Curable Composition Reference | Adduct Formula | Amount Adduct | Cure Times | | | |
|---|---|---|---|---|---|---|
| | | | at 150°C. minutes | at 100°C. minutes | at 50°C. hours | RT days |
| A. | (III) | 0.0016 mole | 3 | <10 | 3–4 | 6 |
| B. | (III) | 0.0032 mole | 3 | 10 | >6 | 14 |
| C. | (IV) | 0.0016 mole | 3.5 | <10 | >6 | 18 |
| D. | (IV) | 0.0032 mole | 4 | 13 | 8–24 | 63 |
| E. | 85% (IV), 15% (V)** | 0.0016 mole | 3.5 | <10 | >6 | 16 |
| F. | 85% (IV), 15% (V)** | 0.0032 mole | 4.5 | 13 | 8–24 | 50 |
| G. | (V) | 0.0016 mole | 2.5 | <10 | 2 | 1.2 |
| H. | (V) | 0.0032 mole | 3 | 10 | 3.5 | 6 |

Table D-continued

| Curable Composition Reference | Adduct Formula | Amount Adduct | Cure Times at 150°C. minutes | at 100°C. minutes | at 50°C. hours | RT days |
|---|---|---|---|---|---|---|
| I. | 56% (III), 33% (IV), 5% (V)*** | 2%*** | — | — | — | >108 |
| J. | 56% (III), 33% (IV), 5% (V)*** | 4%*** | — | — | — | >108 |
| K. | (III) | 2%*** | — | — | — | >108 |
| L. | (III) | 2%*** | — | — | — | >108 |

**Percent is mole percent.
***Percent is weight percent.

That which is claimed is:
1. A polyorganosiloxane consisting essentially of from 3 to 10 siloxane units in which
   a. at least one siloxane unit is selected from the group consisting of RHSiO and $R_2HSiO_{0.5}$ and b. at least one siloxane unit is selected from the group consisting of

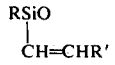

and

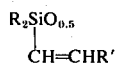

where the sum of siloxane units in (a) and (b) is equal to at least three siloxane units,
   c. any remaining siloxane units being selected from the group consisting of $R_3SiO_{0.5}$, $SiO_2$ and $RSiO_{1.5}$ where each siloxane unit of (c) does not exceed three siloxane units,
      where R is a monovalent radical selected from the group consisting of hydrocarbon radicals and perfluoroalkylethylene radicals, both having no more than six carbon atoms and R' is a monovalent hydrocarbon radical having a secondary or tertiary hydroxy substitution and having no more than ten carbon atoms.
2. The polyorganosiloxane of claim 1 in which there are at least 5 siloxane units, (a) is RHSiO, (b) is

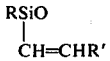

c. is two siloxane units of $R_3SiO_{0.5}$ and R' has tertiary hydroxy substitution.
3. The polyorganosiloxane of claim 2 in which R' is

-C(CH₃)₂OH.

4. The polyorganosiloxane of claim 3 in which R is methyl.
5. The polyorganosiloxane of claim 4 in which there are two RHSiO units and one

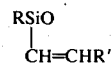

unit.
6. The polyorganosiloxane of claim 4 in which there are one RHSiO unit and two

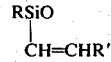

units.
7. A curable organosilicon composition comprising
   1. an organosilicon polymer having an average of from one to three groups per silicon atom selected from the group consisting of monovalent hydrocarbon radicals, aliphatic-unsaturation free monovalent halohydrocarbon radicals, and cyanoalkyl radicals, there being an average per molecule of (1) of at least two monovalent hydrocarbon radicals containing aliphatic unsaturation, the remaining valences of the silicon atoms of said organosilicon polymer being satisfied by divalent radicals selected from the group consisting of divalent oxygen atoms, divalent hydrocarbon radicals, divalent hydrocarbon ether radicals and divalent haloarylene radicals, said divalent radicals linking silicon atoms,
   2. an organosilicon compound containing silicon-bonded hydrogen atoms, there being in addition an average of up to two monovalent organic radicals per silicon atom selected from the group consisting of monovalent hydrocarbon radicals free of aliphatic unsaturation, monovalent halohydrocarbon radicals free of aliphatic unsaturation and cyanoalkyl radicals, the remaining valences of the silicon atoms being satisfied by divalent radicals selected from the group consisting of divalent oxygen atoms, divalent hydrocarbon radicals free of aliphatic unsaturation, divalent hydrocarbon ether radicals and divalent haloarylene radicals, said divalent radicals linking silicon atoms, there being an average of at least two silicon-bonded hydrogen atoms per molecule of (2), the sum of the average number of aliphatic unsaturated monovalent radicals per molecule of (1) and the average number of silicon-bonded hydrogen atoms per molecule of (2) being at least 4,
   3. a platinum catalyst in an amount of at least 0.1 part by weight platinum per one million parts by weight of the combined weights of (1) and (2), and 4. a polyorganosiloxane in an amount to effectively retard the cure at ambient temperatures, said polyorganosiloxane consisting essentially of from 3 to 10 siloxane units in which a. at least one siloxane unit is selected from the group consisting of $RHSiO$ and $R_2HSiO_{0.5}$ and b. at least one siloxane unit is selected from the group consisting of $$\underset{\mathrm{CH=CR'}}{RSiO} \quad \text{and} \quad \underset{\mathrm{CH=CHR'}}{R_2SiO_{0.5}}$$

where the sum of siloxane units in (a) and (b) is equal to at least three siloxane units, c. any remaining siloxane units being selected from the group consisting of $R_3SiO_{0.5}$, $SiO_2$ and $RSiO_{1.5}$ where each siloxane unit of (c) does not exceed three siloxane units, where R is a monovalent radical selected from the group consisting of hydrocarbon radicals and perfluoroalkylethylene radicals, both having no more than six carbon atoms and R' is a monovalent hydrocarbon radical having a secondary or tertiary hydroxy substitution and having no more than ten carbon atoms.

8. The curable organosilicon composition according to claim 7 wherein (1) is a triorganosiloxy-endblocked polydiorganosiloxane having a viscosity of at least 100 cs. at 25°C.

9. The curable organosilicon composition according to claim 8 wherein the organo radicals of (1) are methyl and vinyl.

10. The curable organosilicon composition according to claim 8 wherein the organo radicals of (1) are methyl, phenyl and vinyl.

11. The curable organosilicon composition according to claim 7 wherein the polyorganosiloxane (4) is present in an amount of at least one mole of polyorganosiloxane (4) per mole of platinum.

12. The curable organosiloxane composition according to claim 11 wherein the polyorganosiloxane (4) is present in an amount of 0.5 to 3 weight percent based on the total weight of the composition.

13. The curable organosilicon composition according to claim 7 wherein the polyorganosiloxane (4) has at least 5 siloxane units, (a) is RHSiO, (b) is $$\underset{\mathrm{CH=CHR'}}{RSiO,}$$

c. is two siloxane units of $R_3SiO_{0.5}$ and R' has tertiary hydroxy substitution.

14. The curable organosilicon composition according to claim 13 in which R' is $-C(CH_3)_2OH$.

15. The curable organosilicon composition according to claim 14 in which R is methyl.

16. The curable organosilicon composition according to claim 15 in which there are two RHSiO units and one $$\underset{\mathrm{CH=CHR'}}{RSiO}$$

unit.

17. The curable organosilicon composition according to claim 15 in which there are one RHSiO unit and two $$\underset{\mathrm{CH=CHR'}}{RSiO}$$

units.

18. The curable organosilicon composition according to claim 8 wherein the polyorganosiloxane (4) is present in an amount of at least one mole of polyorganosiloxane (4) per mole of platinum.

19. The curable organosilicon composition according to claim 18 wherein the polyorganosiloxane (4) is present in an amount of 0.5 to 3 weight percent based on the total weight of the composition.

20. The curable organosilicon composition according to claim 19 wherein the polyorganosiloxane (4) has at least 5 siloxane units, (a) is RHSiO, (b) is $$\underset{\mathrm{CH=CHR'}}{RSiO,}$$

c. is two siloxane units of $R_3SiO_{0.5}$ and R' has tertiary hydroxy substitution.

21. The curable organosilicon composition according to claim 20 in which R' is $-C(CH_3)_2OH$.

22. The curable organosilicon composition according to claim 21 in which R is methyl.

23. The curable organosilicon composition according to claim 22 in which there are two RHSiO units and one $$\underset{\mathrm{CH=CHR'}}{RSiO}$$

unit.

24. The curable organosilicon composition according to claim 22 in which there are one RHSiO unit and two $$\underset{\mathrm{CH=CHR'}}{RSiO}$$

units.

25. The curable organosilicon composition according to claim 23 in which the radicals of (1) are methyl, phenyl and vinyl.

26. The curable organosilicon composition according to claim 24 in which the radicals of (1) are methyl, phenyl and vinyl.

* * * * *

UNITED STATES PATENT AND TRADEMARK OFFICE
CERTIFICATE OF CORRECTION

PATENT NO. : 3,989,667
DATED : November 2, 1976
INVENTOR(S) : Chi-Long Lee; Ollie W. Marko It is certified that error appears in the above-identified patent and that said Letters Patent are hereby corrected as shown below:

In Column 6, line 43; the formula reading "$-CH_2CH=CHCH_2-$, $-CH_2C\ \ CCH_2-$," should read "$-CH_2CH=CHCH_2-$, $-CH_2C\equiv CCH_2-$,"

In Column 8, line 33; the formula reading "$-CH_2CH_2OCH\ \ 2CH_2-$," should read "$-CH_2CH_2OCH_2CH_2-$,"

In Column 9, line 27; the formula reading "$PtCl_2\{P(CH_2CH_2CH_3)_3\}_2$," should read "$PtCl_2\{P(CH_2CH_2CH_3)_3\}_2$,"

In Column 9, line 31; the formula reading "$Pt(CH_3CH)_2Cl_2$, $\{Pt(CH_3CN)_2(CH_3)_4\}Cl_2$," should read "$Pt(CH_3CN)_2Cl_2$, $\{Pt(CH_3CN)_2(CH_3)\}_4Cl_2$,"

In Column 9, line 38; the formula reading "$PtCl_2 \cdot PCl_3$, $\{Pt(NH_3)_4 \cdot PtCl_4\}$, should read "$PtCl_2 \cdot PCl_3$, $\{Pt(NH_3)_4\} \cdot \{PtCl_4\}$,"

UNITED STATES PATENT AND TRADEMARK OFFICE
CERTIFICATE OF CORRECTION

PATENT NO. : 3,989,667
DATED : November 2, 1976
INVENTOR(S) : Chi-Long Lee; Ollie W. Marko It is certified that error appears in the above-identified patent and that said Letters Patent are hereby corrected as shown below:

In Column 9, line 59; the line reading "rate of cure at room temperature of completely pre-" should read "rate of cure at room temperature or completely pre-"

In Column 11, line 13; the formula reading "$\equiv SiH + CH_2 = CH-CH_2Si\equiv \xrightarrow{(Pt)} \equiv SiCH_2CH_2CH_2CH_2Si\equiv$" should read "$\equiv SiH + CH_2 = CH-CH_2Si\equiv \xrightarrow{(Pt)} \equiv SiCH_2CH_2CH_2Si\equiv$"

In Column 13, line 55; the formula reading

"$CH_3SiO \quad OH$
$\quad\quad CH=CHCCH_2CHCH_3$
$\quad\quad\quad\quad CH_3 \quad CH_3$"

should read

"$CH_3SiO \quad OH$
$\quad\quad CH=CHCCH_2CHCH_3$
$\quad\quad\quad\quad CH_3 \quad CH_3$"

Signed and Sealed this

Eighth Day of December 1981

[SEAL]

Attest:

GERALD J. MOSSINGHOFF

Attesting Officer — Commissioner of Patents and Trademarks